United States Patent [19]

Sturm

[11] Patent Number: 4,837,438
[45] Date of Patent: Jun. 6, 1989

[54] DIRECT INFRARED MEASUREMENT OF HOMOGENOUS MIXTURES

[75] Inventor: Steven P. Sturm, Columbus, Ohio

[73] Assignee: Process Automation Business, Inc., Columbus, Ohio

[21] Appl. No.: 62,992

[22] Filed: Jun. 17, 1987

[51] Int. Cl.$^4$ .......................................... G01N 21/35
[52] U.S. Cl. ..................................... 250/339; 250/341
[58] Field of Search .............................. 250/339, 341

[56] References Cited

U.S. PATENT DOCUMENTS

| | | | |
|---|---|---|---|
| 3,076,723 | 2/1963 | Covington | 117/93.31 |
| 3,448,268 | 6/1969 | Proctor | 250/83.3 |
| 4,300,049 | 11/1981 | Sturm | 250/339 |
| 4,363,968 | 12/1982 | McGowan et al. | 250/339 |
| 4,577,104 | 3/1986 | Sturm | 250/341 |
| 4,582,520 | 4/1986 | Sturm | 250/339 |
| 4,755,678 | 7/1988 | Izatt et al. | 250/339 |

Primary Examiner—Carolyn E. Fields
Assistant Examiner—John A. Miller
Attorney, Agent, or Firm—John H. Mulholland

[57] ABSTRACT

Apparatus and associated methods for measuring the polymer content of a mixture having polymer and cellulose components. Infrared absorption means are employed to derive a measurement of that fraction of the combined weights of polymer and cellulose components which is accounted for by the polymer.

11 Claims, 4 Drawing Sheets

DIRECT INFRARED MEASUREMENT OF HOMOGENOUS MIXTURES

BACKGROUND OF THE INVENTION

1. Technical Field

This invention relates generally to measuring the polymer content of a material which has both polymer and cellulose components. More particularly, the invention relates to apparatus and associated methods for measuring the polymer fraction of the polymer and cellulose components by infrared absorption means.

2. Description of the Background Art

Specialty papers for use in producing such items as teabags, non-woven cloth, and other products are predominately composed of a fibrous polymer/cellulose homogeneous mixture. The polymers are added to produce qualities, such as strength, that are inadequate in other papers. Accurately measuring the polymer content of these specialty papers is an important step in controlling product quality and cost.

Previous attempts at on-line measurement of polymer content have employed radiation absorption methods wherein the absorptances of two radiation wavelengths, one of which is sensitive to the polymer, are gauged and electronically quantified, and the corresponding electronic signals appropriately processed, to measure polymer weight per unit area directly. However, these systems sometimes can provide only a crude indication of whether the polymer content of the mixture is consistent with the desired physical quality of the paper sheet. Such is the case, for example, when the primary purpose of the polymer is to bind the cellulose fibers to produce a desired degree of strength in a paper. In that case, the polymer weight (Hereinafter, the word "weight", as applied to polymer, cellulose, or both, is intended to mean weight per unit area.) by itself cannot effectively serve as a measurement of strength since it does not take into account the weight of cellulose with which the polymer is combined. Accordingly, an on-line measurement of the polymer fraction of combined polymer and cellulose weights would correlate better with laboratory tests of the physical quality than would an on-line measurement of mere polymer weight.

SUMMARY OF THE INVENTION

This invention provides apparatus and associated processes for measuring the polymer fraction of the polymer and cellulose components of a mixture. Typically, the measurement is made during continuous production of the mixture, and the mixture is in the form of a fibrous sheet.

Infrared radiation is directed from a source onto a portion of the mixture. Two sets of infrared radiation wavelengths are detected after the radiation has interacted with the mixture. A first set includes wavelengths having about the same absorption coefficient for the cellulose component of the mixture, but having substantially different absorption coefficients for the polymer component. A second set includes wavelengths having about the same absorption coefficient for the polymer component, but having substantially different absorption coefficients for the cellulose component. The detection system produces responses to the radiation corresponding to the two sets. These responses are processed to produce a measurement of that fraction of the combined polymer and cellulose components which is accounted for by the polymer. The resulting polymer-fraction measurement correlates better than existing measurements of polymer content with the results of standard strength tests for specialty papers.

DESCRIPTION OF THE PREFERRED EMBODIMENT

Figure 1:
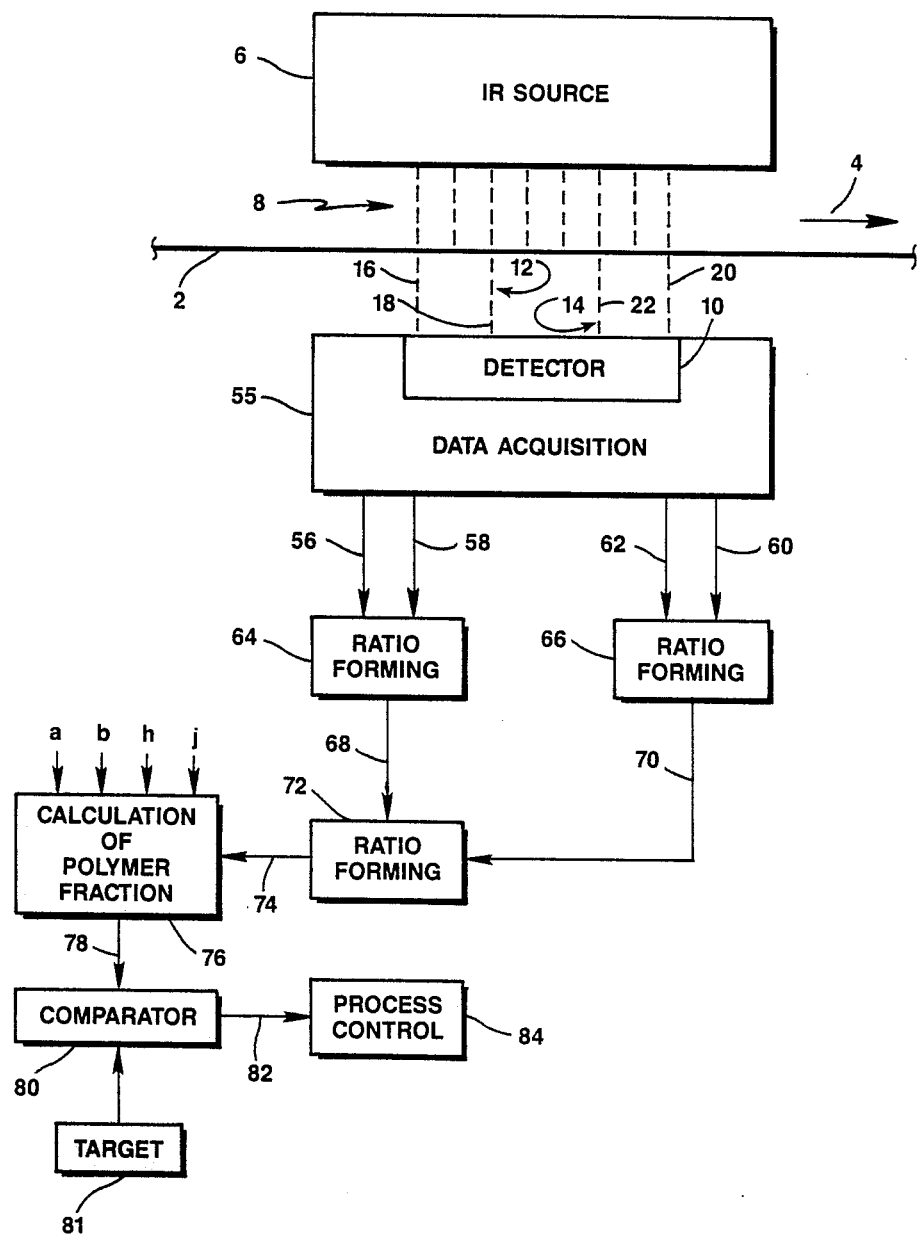
FIG. 1 is a schematic illustration of an embodiment of the invention, combining both representations of typical structural elements and representations of typical information handling procedures.

Referring to FIG. 1, the numeral 2 designates a sheet of material, typically a specialty paper having both polymer and cellulose components, that is under inspection during continuous production thereof. The illustrated portion of the sheet 2 can be viewed as moving in the direction indicated by the arrow 4.

The fraction of the combined weights of polymer and cellulose components which is accounted for by the polymer (herein termed the "polymer fraction") is measured by an infrared radiation gauging apparatus comprising a source means 6 for directing infrared radiation (as indicated at 8) onto a portion of the sheet 2, and a detector means 10 for detecting two sets 12, 14 of infrared radiation wavelengths transmitted through the sheet.

The first set 12 may include wavelengths 16 at about 2.10 microns and wavelengths 18 at about 2.38 microns. The second set 14 may include wavelengths 20 at about 2.10 microns and wavelengths 22 at about 1.80 microns.

Figure 2:
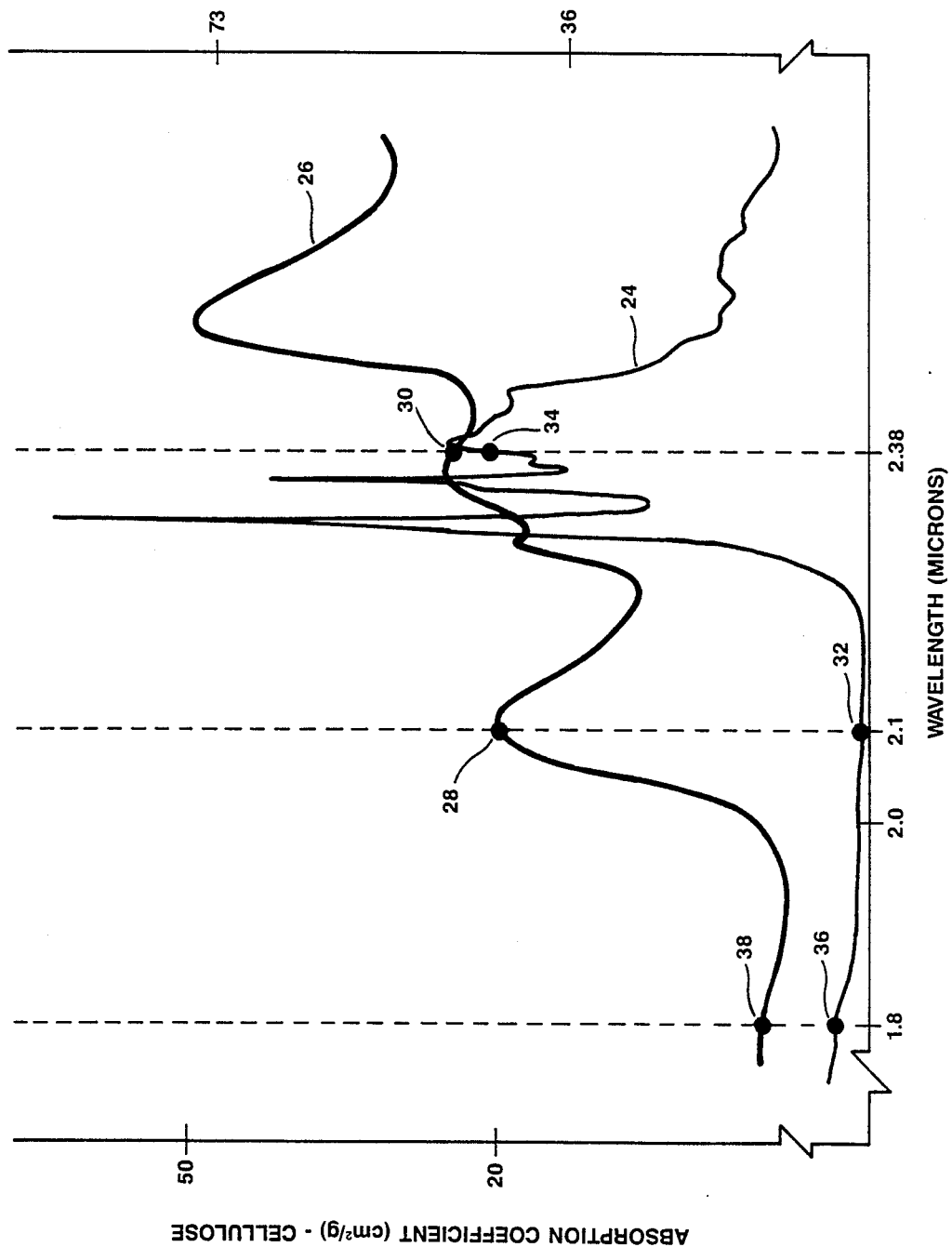
FIGS. 2 through 4 are plots of infrared absorption coefficients for polymers and cellulose, as functions of wavelength, illustrating the selection of wavelengths in accordance with the preferred embodiment.

In FIG. 2, the curve 24 shows the absorption coefficient of polyethylene (in square centimeters per gram) as a function of infrared wavelength in microns. Curve 26 shows the same relation for cellulose. The first set 12 of wavelengths 16, 18 is selected, as at points 28 and 30, to have about the same absorption coefficient for cellulose, but to have, as indicated at points 32 and 34, substantially different absorption coefficients for polyethylene. The second set 14 of wavelengths 20, 22 is selected, as at points 36 and 32, to have about the same absorption coefficients for polyethylene, but to have, as indicated at points 38 and 28, substantially different absorption coefficients for cellulose.

Figure 3:
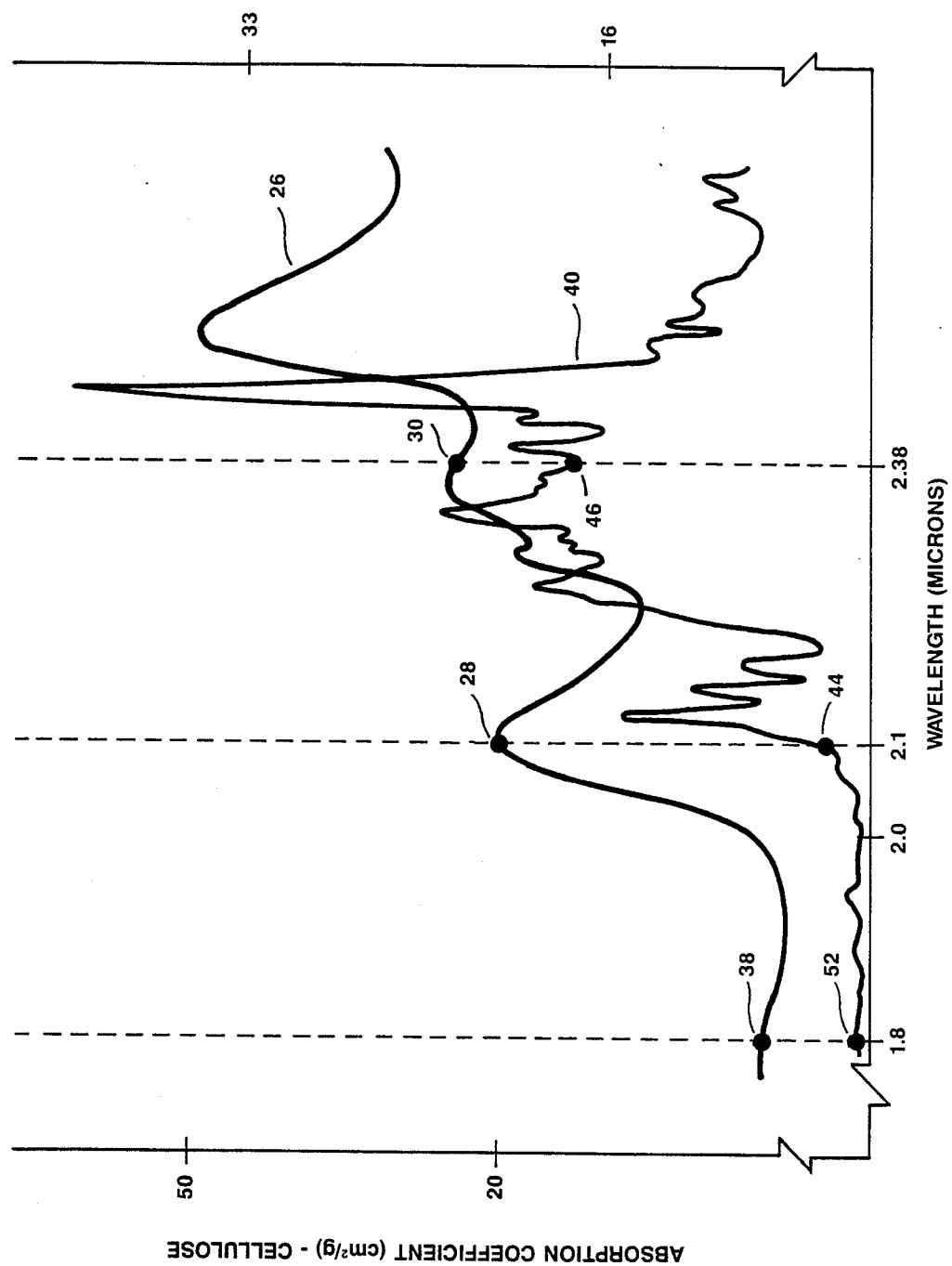
Figure 4:
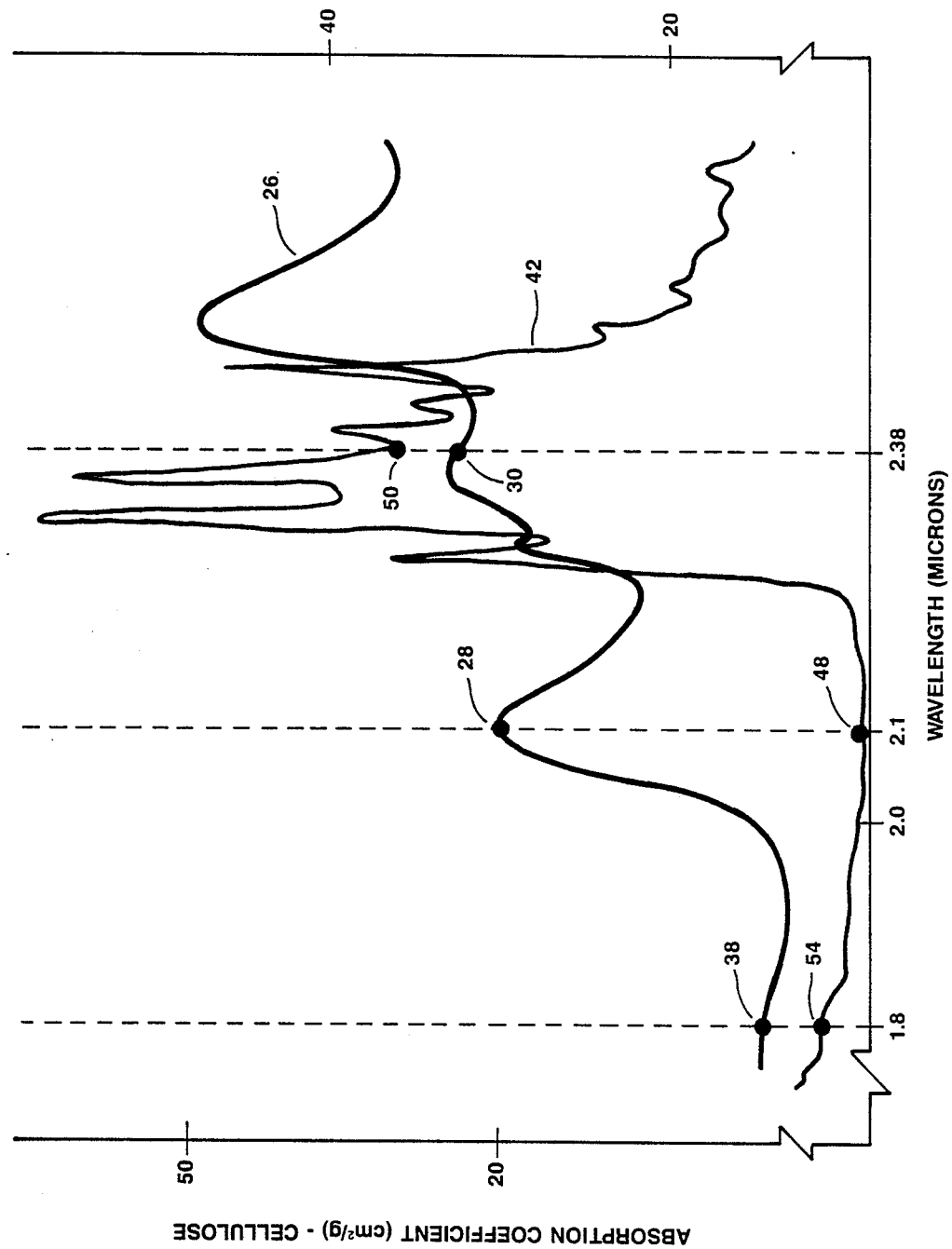

In similar fashion, FIGS. 3 and 4 show (as curves 40 and 42) the absorption coefficients for polyester and polypropylene, respectively, as functions of infrared wavelength, and also show curve 26 for cellulose. The first set 12 of wavelengths 16, 18 is indicated as points 28 and 30 on curve 26. These correspond to points 44 and 46 on curve 40 or to points 48 and 50 on curve 42. The second set 14 of wavelengths 20, 22 is indicated as points 38 and 28 on curve 26. These correspond to points 52 and 44 on curve 40 or to points 54 and 48 on curve 42.

The above-prescribed wavelengths for the first and second sets 12, 14 corresponding to each polymer are of course not exclusive, since many combinations of wavelengths will satisfy the requirements that the first set include wavelengths that have about the same absorption coefficient for the cellulose component but have substantially different absorption coefficients for the polymer component, and that the second set of wavelengths have about the same absorption coefficient for the polymer component but have substantially different absorption coefficients for the cellulose component. Although these requirements are satisfied by the selection of three different wavelengths for the above illustrated cases, one may employ four different wavelengths where necessary or desirable, as exemplified in FIG. 2 of U.S. Pat. No. 4,577,104.

A similar wavelength selection process may be used for other polymers where it is desired to measure the weight of the polymer as a fraction of the combined weight of polymer and cellulose. It will be recognized that the wavelengths should be selected so that, for the mixture in question, none of the wavelengths is subject to significant absorption by components other than the polymer and cellulose. For example, where the mixture is in the form of a homogeneous sheet of specialty paper as mentioned above, it will typically have some water content, and it will therefore be best not to select wavelengths around 1.92 microns so as to avoid the necessity of correcting for the effect of absorption by water.

Referring again to FIG. 1, wavelengths 16, 18, 20 and 22 are shown to be detected by the detector 10. The detection of selected wavelengths may be accomplished, for example, by mounting appropriate filters in a modulating wheel (not shown) as exemplified in U.S. Pat. No. 4,300,049, or by employing a four-channel detector with separate filters for wavelengths 16, 18, 20, and 22, as described in pending application Ser. No. 885,017. The detector 10 is part of a data acquisition system 55, and produces detector responses (not shown)—typically in the form of analog signals—that can be processed to produce measurements of polymer fraction for the sheet 2. System 55, which may be similar to apparatus described in U.S. Pat. No. 4,300,049, produces responses 56, 58, 60, and 62 that express the transmittances of wavelengths 16, 18, 20, and 22, respectively. Each transmittance value represents the ratio of the radiation intensity transmitted to the detector 10 with the sheet 2 in position, to the radiation intensity transmitted to the detector in the absence of the sheet. The transmittance values expressed by responses 56, 58, 60, and 62 are communicated to first and second ratio forming operations 64 and 66, respectively.

At 64, a function of the transmittances of radiation wavelengths in the first set 12 is formed to produce a first response 68 to the polymer contained in the sheet 2. The first response is typically represented mathematically as follows (For purpose of description, it is assumed that polypropylene is the polymer of interest.):

$$(X/Y)-1 = a*(P+jC)*f(S), \quad (1)$$

where X is the transmittance at the polymer reference wavelength of 2.1 microns; Y is the transmittance at the polymer absorption wavelength of 2.38 microns; "a" is a constant determined during calibration; P is the weight of the polymer contained in the sheet 2; C is the weight of the cellulose contained in the sheet; "j" is a multiplier accounting for partial sensitivity to cellulose; (The multiplier "j" is present because, even though the best selection of wavelengths may have been made to provide cellulose independence in the polymer measurement, it may not be possible in every case to balance the effect of the cellulose.); and f(S) is a first error function that is dependent upon physical properties of the polymer and cellulose fibers (such as diameter and length) which will affect their optical scattering capabilities. This error is attributable to the change in path length resulting from the scattering media, as described by the Kubelka-Munk theory.

At 66, a function of the transmittances of radiation in the second set 14 is formed to produce a second response 70 to the cellulose contained in the sheet 2. The second response 70 is typically represented mathematically as follows:

$$(V/Z)-1 = b*(C+hP)*f(S), \quad (2)$$

where V is the transmittance at wavelength 1.80 microns; Z is the transmittance at wavelength 2.10 microns; "b" is a constant determined during calibration; f(S) is the first error function as in equation 1; and "h" is a multiplier accounting for partial sensitivity to the polymer. The multiplier "h" is included because, even though the best possible selection of wavelengths may have been made to provide polymer independence in the cellulose measurement, it may not be possible in every case to balance the effect of the polymer. In FIG. 3, for example, small variations in the band picked at 28 and 44 will cause polymer dependence in the cellulose measurement.

A third ratio forming operation 72 forms a function of the ratio of the first and second responses 68, 70 to produce a third response 74 having a magnitude T that is substantially independent of the first error function f(C), but is dependent on the second error function hP. The third response 74 may be represented mathematically as follows:

$$T=[a*(P+jC)]/[(b*(C+hP)]. \quad (3)$$

It should be noted that this is the ratio of the first response 68 to the second response 70. The combined weight of the polymer and cellulose components of the sheet 2 is equal to the sum P + C. Therefore, expression 3 may be rewritten as follows:

$$T=(a/b)* [(\%P+j*\%C)/(\%C+h*\%P)], \quad (4)$$

where %P is the polymer fraction or percent polymer, and %C is the cellulose fraction or percent cellulose.

Since %C=1−%P, $$T=(a/b)*[(\%P+j-j*\%P)/(h*\%P+1-\%P)]. \quad (5)$$

Letting (a/b) equal d, $$\%P=(dj-T)/[T(h-1)-d(1-j)]. \quad (6)$$

As illustrated in FIG. 1, the calculation of polymer fraction is implemented at 76 where the third response 74 is used in conjunction with calibration data a, b, j, and h to produce a direct measurement response 78 expressive of the polymer fraction of the sheet 2, and substantially independent of the first error function f(S).

In calibrating the apparatus, an iterative digital computer program is typically used to determine the values for the calibration data a, b, j and h which make equation 6 best fit laboratory-determined polymer fraction values for a number of actual samples of the material being measured.

Measurement responses 78 may be delivered to a comparator 80 wherein the responses are compared to a target polymer fraction value (indicated as 81). In response to a deviation from the target value 81, adjustment signals 82 may be communicated to a process control unit 84, which may be any conventional unit for controlling the rate at which cellulose or polymer is delivered for formation of the sheet 2.

While the invention has been described in terms of the preferred embodiment, the description is not intended to restrict the scope of the invention beyond that defined by the following claims and their equivalents.

What is claimed is:

1. An apparatus for directly measuring the polymer content of a homogeneous mixture having both polymer and cellulose components, comprising:
   (a) source means for directing infrared radiation onto a portion of the mixture;
   (b) detector means for detecting infrared radiation of two sets of wavelengths after the radiation has interacted with the mixture, the first set including wavelengths that have about the same absorption coefficient for the cellulose component but have substantially different absorption coefficients for the polymer component, the second set including wavelengths that have about the same absorption coefficient for the polymer component but have substantially different absorption coefficients for the cellulose component, the detector means produces detector responses to the radiation corresponding to the two sets, wherein the responses are processed to produce a measurement of the fraction of polymer and cellulose components which is accounted for by the polymer component.

2. An apparatus as in claim 1 further comprising means for processing the detector responses to produce a measurement of the polymer fraction.

3. An apparatus as in claim 2 wherein the processing means employs first, second, and third ratio forming operations, the first ratio forming operation forming a function of the transmittances of radiations in the first set to form a first response, the second ratio forming operation forming a function of the transmittances of radiations in the second set to produce a second response, and the third ratio forming operation forming a function of the ratio of the first and second responses to produce a third response that is used in conjunction with calibration data to produce a measurement response expressive of the polymer fraction of the mixture.

4. An apparatus as in claim 3 wherein the first set includes wavelengths of about 2.38 microns and about 2.10 microns, and the second set includes wavelengths of about 1.80 microns and 2.10 microns.

5. A method for directly measuring the polymer content of a homogeneous mixture having both polymer and cellulose components, comprising the steps of:
   (a) directing infrared radiation from a source thereof onto a portion of the mixture;
   (b) detecting infrared radiation of two sets of wavelengths after the radiation has interacted with the mixture, the first set having about the same absorption coefficient for the cellulose component but having substantially different absorption coefficients for the polymer component, the second set having about the same absorption coefficient for the polymer component but having substantially different absorption coefficients for the cellulose component, to produce detector responses for each wavelength of the two sets;
   (c) processing the detector responses to produce a measurement response expressive of the fraction of polymer and cellulose components which is accounted for by the polymer component.

6. A method as in claim 5 wherein the steps are performed during continuous production of the mixture.

7. A method as in claim 6 wherein the mixture is in the form of a sheet of paper.

8. A method as in claim 7 further comprising the step of comparing the measurement response to a target polymer fraction value.

9. A method as in claim 8 further comprising the step of communicating adjustment signals to a process control unit in response to deviations of the measurement response from the target polymer fraction value.

10. A method as in claim 9 further comprising the step of controlling the polymer fraction of the sheet in response to the adjustment signals.

11. A method as in claim 10 wherein the first set includes wavelengths of about 2.38 microns and about 2.10 microns and the second set includes wavelengths of about 1.80 microns and about 2.10 microns.

* * * * *